United States Patent [19]
Casci et al.

[11] Patent Number: 4,537,754
[45] Date of Patent: Aug. 27, 1985

[54] ZEOLITE EU-1 AND A METHOD OF MAKING ZEOLITE EU-1

[75] Inventors: John L. Casci, Redcar; Barrie M. Lowe, Edinburgh; Thomas V. Whittam, Darlington, all of England

[73] Assignee: Imperial Chemical Industries PLC, London, England

[21] Appl. No.: 272,465

[22] Filed: Jun. 11, 1981

[30] Foreign Application Priority Data

Jun. 12, 1980 [GB] United Kingdom ............... 8019210

[51] Int. Cl.³ .................. C01B 35/10; C01B 33/28; C01B 33/20
[52] U.S. Cl. .................. 423/277; 423/326; 423/328; 423/329; 423/330; 423/331; 423/332; 502/60; 502/61; 502/62; 502/77; 502/202
[58] Field of Search .......... 423/328, 329, 118, 328 T, 423/329 T, 326, 330–332; 252/431 N, 455 Z; 502/77, 202, 60–62, 277

[56] References Cited

U.S. PATENT DOCUMENTS 3,702,886 11/1972 Argauer et al. .................. 423/328
3,709,979 1/1973 Chu .................. 423/328 T
3,832,449 8/1974 Rosinski et al. .................. 423/329
4,061,717 12/1977 Kerr et al. .................. 252/455 Z
4,076,842 2/1978 Plank et al. .................. 423/328
4,086,186 4/1978 Rubin et al. .................. 423/328 T
4,108,881 8/1978 Rollmann et al. .................. 423/328 T
4,180,689 12/1979 Davies et al. .................. 423/329
4,229,424 10/1980 Kokotailo .................. 423/328 T
4,299,732 11/1981 Ball et al. .................. 423/328

FOREIGN PATENT DOCUMENTS 0000669 2/1979 European Pat. Off. .
0007081 1/1980 European Pat. Off. .
1193254 5/1970 United Kingdom .

Primary Examiner—Gary P. Straub
Assistant Examiner—Jackson Leeds
Attorney, Agent, or Firm—Cushman, Darby & Cushman

[57] ABSTRACT

A new zeolite material designated EU-1 having a molar composition expressed by the formula:

0.5 to 1.5 $R_2O:Y_2O_3$: at least 10 $XO_2$:0 to 100 $H_2O$ wherein R is a monovalent cation or $1/n$ of a cation of valency n, X is silicon and/or germanium, Y is one or more of aluminum, iron, gallium or boron, and $H_2O$ is water of hydration additional to water notionally present when R is H, and having an X-ray pattern substantially as set out in Tables 1 and 2 is prepared from a reaction mixture containing $XO_2$ (preferably silica), $Y_2O_3$ (preferably alumina) and a dicationic alkylated polymethylene diamine. The new zeolite is useful in catalytic processes, especially xylenes isomerization.

13 Claims, 1 Drawing Figure

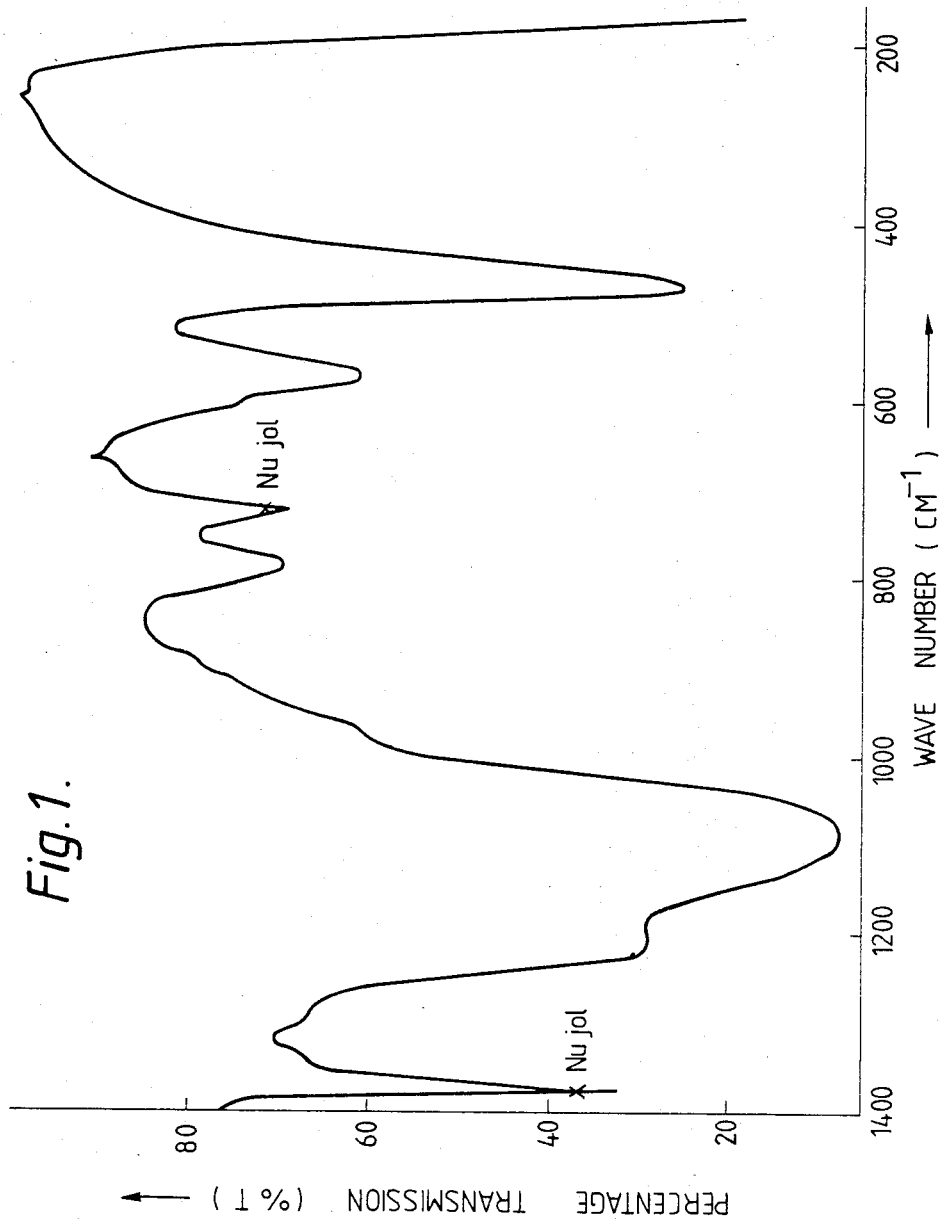

drawn with the relationship between the aforesaid ZSM-23 family of zeolites and the ZSM-5/ZSM-11 family of zeolites (as described, for example in U.S. Pat. Nos. 3,702,886 and 3,709,979; and in Nature, 1978, 275, 119), which from the literature appear to have similar X-ray diffraction data, but in fact have related, but significantly different, three dimensional frameworks.

Zeolite EU-1 has molecular sieve properties analogous to those of known zeolites. Thus zeolite EU-1 may be characterised by its adsorption capacity for molecules of various sizes. Typical results are shown in Table 3. Slight sorption of cyclohexane and rapid sorption of p-xylene suggest an entry port size of about 6.0 A in diameter. The results given in Table 3 also show that m-xylene is sorbed more slowly than p-xylenes, thereby indicating that zeolite EU-1 may be used to separate xylene isomers. It will also be seen from Table 3 that zeolite EU-1 has significant hydrophobic voidage, the voids volume available for water being only 6.9 cc per 100 g as compared with 14.4 cc per 100 g for n-hexane and 12.4 cc per 100 g for p-xylene. This means that zeolite EU-1 is a useful sorbent for removing hydrocarbons from wet gas or from aqueous effluents.

TABLE 3

| Adsorbate | Sorption at 25° C. | | | | |
|---|---|---|---|---|---|
| | Kinetic* Diameter $\sigma A$ | Pressure mm Hg | Time Hours | Wt sorbed g/100 g | Voidage available cc/100 g |
| Water | 2.7 | 4.5 | 2 | 6.9 | 6.9 |
| | 2.7 | 4.5 | 16 | 11.0 | 11.0 |
| n-hexane | 4.3 | 45.8 | 2 | 9.5 | 14.4 |
| p-xylene | 5.8 | 1.6 | 2 | 10.5 | 12.1 |
| | 5.8 | 1.6 | 18.5 | 10.6 | 12.2 |
| m-xylene | 5.9 | 1.6 | 2 | 2.3 | 2.6 |
| | | | 18.5 | 5.5 | 6.3 |
| cyclohexane | 6.0 | 2.7 | 2 | 1.1 | 1.4 |
| | | | 18.5 | 1.1 | 1.4 |

*Lennard Jones kinetic diameter
see D W Breck "Zeolite Molecular Sieves", Wiley Interscience, 1974 p 636

Zeolite EU-1 is further characterised by its infrared spectrum (shown in FIG. 1). In common with other zeolites, zeolite EU-1 has two main IR absorption regions, viz. the stretch $\nu$ of the Si-O situated near to 1100 cm$^{-1}$ and the deformation $\delta$ of the Si-O situated near to 500 cm$^{-1}$.

Referring to the absorption near to 1100 cm$^{-1}$, zeolite EU-1 has absorptions at 1213 cm$^{-1}$ (medium weak intensity) and at 1080 cm$^{-1}$ (very strong). By comparison, the absorptions near 1100 cm$^{-1}$ for zeolites ZSM-5 and ZSM-11 are 1228 cm$^{-1}$ (medium) and 1095 cm$^{-1}$ (very strong) for ZSM-5, and 1221 cm$^{-1}$ (medium strong) and 1090 cm$^{-1}$ (very strong) for ZSM-11. Thus there are small but significant differences both in position and intensity of the absorption of zeolite EU-1 as compared with the absorptions of ZSM-5 and ZSM-11.

The deformation $\delta$ near to 500 cm$^{-1}$ of EU-1 has a medium intensity absorption band which is a doublet centred at 570 cm$^{-1}$ and which is much weaker than the band at 470 cm$^{-1}$. By comparison, ZSM-11 has a doublet which is symmetrically shaped with absorption occurring at 548 cm$^{-1}$ and 448 cm$^{-1}$ ZSM-5 has a doublet absorption band at 545 cm$^{-1}$ and a second band at 455 cm$^{-1}$. Thus EU-1 is similar to ZSM-5 in that the higher absorption centered at 570 cm$^{-1}$ is a doublet. However, the shifts in position, number and relative intensities of the absorptions at 500 cm$^{-1}$ (and at 1100 cm$^{-1}$ as described above) are sufficient to identify EU-1 and to distinguish it from ZSM-5 and ZSM-11.

The invention provides also a method of making zeolite EU-1 which comprises reacting an aqueous mixture comprising at least one oxide $XO_2$, at least one oxide $Y_2O_3$ and at least one alkylated derivative of a polymethylene $\alpha$-$\omega$ diamine having the formula

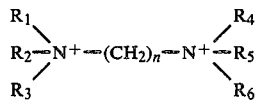

which by our definition is $Q^{2+}$ an amine degradation product thereof, or a precursor thereof, wherein n is in the range from 3 to 12 and $R_1$ to $R_6$ which may be the same or different, can be alkyl or hydroxyalkyl groups, containing from 1 to 8 carbon atoms and up to five of the groups $R_1$-$R_6$ can be hydrogen, the mixture having the molar composition:

| $XO_2/Y_2O_3$ | at least 10, preferably 10 to 150 |
|---|---|
| $OH^-/XO_2$ | 0.1 to 6.0 preferably 0.1 to 1.0 |
| $(M^+ + Q)/Y_2O_3$ | 0.5 to 100 |
| $Q/(M^+ + Q)$ | 0.1 to 1.0 |
| $H_2O/XO_2$ | 1 to 100 | where X is silicon and/or germanium, Y is one or more of aluminium, iron, gallium, or boron, M is an alkali metal or ammonium, and Q is the aforesaid alkylated derivative of a polymethylene diamine, an amine degradation product thereof, or a precursor thereof, or a related compound.

M and/or Q can be present as hydroxides or salts of inorganic or organic acids provided the $OH^-/XO_2$ requirement is fulfilled.

Preferred alkylated polymethylene diamine starting materials include alkylated hexamethylene diamines, especially methylated hexamethylene diamines, for example 1:6 N,N,N,N$^1$,N$^1$,N$^1$-hexamethyl hexamethylene diammonium salts (e.g. halide, hydroxide, sulphate, silicate, aluminate).

Suitable precursors of the alkylated polymethylene diamine starting materials include the parent diamine along with alcohols or alkyl halides which can be used as such or can be preheated together in the reaction vessel preferably in solution (e.g. in methyl ethyl ketone) prior to addition of the other reactants required for zeolite EU-1 synthesis.

The preferred alkali metal (M) is sodium. The preferred oxide $XO_2$ is silica ($SiO_2$) and the preferred oxide $Y_2O_3$ is alumina ($Al_2O_3$).

The silica source can be any of those commonly considered for use in synthesizing zeolites, for example powdered solid silica, silicic acid, colloidal silica or dissolved silica. Among the powdered silicas usable are precipitated silicas, especially those made by precipitation from an alkali metal silicate solution, such as the type known as "KS 300" made by AKZO, and similar products, aerosil silicas, fume silicas and silica gels suitably in grades for use in reinforcing pigments for rubber or silicone rubber. Colloidal silicas of various particle sizes may be used, for example 10-15 or 40-50 microns, as sold under the Registered Trade Marks "LUDOX", "NALCOAG" and "SYNTON". The usable dissolved silicas include commercially available waterglass silicates containing 0.5 to 6.0, especially 2.0 to 4.0 mols of $SiO_2$ per mol of alkali metal oxide, "active" alkali metal silicates as defined in U.K. Pat. No. 1193254, and sili-

ZEOLITE EU-1 AND A METHOD OF MAKING ZEOLITE EU-1

The present invention relates to a zeolite material, hereinafter referred to as zeolite EU-1, to a method of making it and to processes using it as a catalyst.

According to the present invention we provide zeolite EU-1 having a molar composition expressed by the formula:

0.5 to 1.5 $R_2O:Y_2O_3$:at least 10 $XO_2$:0 to 100 $H_2O$ wherein R is a monovalent cation or 1/n of a cation of valency n, X is silicon and/or germanium, Y is one or more of aluminium, iron, gallium or boron, and $H_2O$ is water of hydration additional to water notionally present when R is H, and having an X-ray pattern substantially as set out in Tables 1 and 2 (as determined by standard technique using copper Kα radiation). Table 1 shows X-ray data for zeolite EU-1 as prepared, and Table 2 shows X-ray data for zeolite EU-1 in the calcined Na-H form. The X-ray pattern is little affected by the type of cation present.

TABLE 1

| Zeolite EU-1 as freshly prepared | |
|---|---|
| d (A) | I/Io |
| 11.03 | Very Strong |
| 10.10 | Strong |
| 9.72 | Weak |
| 6.84 | Weak |
| 5.86 | Very Weak |
| 4.66 | Very Strong |
| 4.31 | Very Strong |
| 4.00 | Very Strong |
| 3.82 | Strong |
| 3.71 | Strong |
| 3.44 | Medium |
| 3.38 | Medium |
| 3.26 | Strong |
| 3.16 | Very Weak |
| 3.11 | Very Weak |
| 2.96 | Very Weak |
| 2.71 | Very Weak |
| 2.55 | Weak |
| 2.48 | Very Weak |
| 2.42 | Very Weak |
| 2.33 | Very Weak |
| 2.30 | Very Weak |
| 2.13 | Very Weak |

TABLE 2

| Zeolite EU-1 in calcined Na—H form | |
|---|---|
| d (A) | I/Io |
| 11.11 | Very strong |
| 10.03 | Very strong |
| 9.78 | Weak |
| 7.62 | Weak |
| 6.84 | Medium |
| 6.21 | Very Weak |
| 5.73 | Weak |
| 4.87 | Very weak |
| 4.60 | Very strong |
| 4.30 | Very strong |
| 3.97 | Very strong |
| 3.77 | Strong |
| 3.71 | Weak |
| 3.63 | Very weak |
| 3.42 | Medium |
| 3.33 | Medium |
| 3.27 | Strong |
| 3.23 | Medium |
| 3.15 | Weak |
| 3.07 | Weak |
| 2.93 | Weak |
| 2.69 | Weak |
| 2.63 | Very weak |
| 2.57 | Very weak |
| 2.51 | Weak |
| 2.45 | Very weak |
| 2.41 | Very weak |
| 2.32 | Very weak |
| 2.29 | Very weak |
| 2.11 | Very weak |

Within the above definition of chemical composition, the number of moles of $XO_2$ is typically in the range 10 to 500 and zeolite EU-1 appears to be most readily formed in a state of high purity when the number of moles of $XO_2$ is in the range 20 to 300.

This definition includes both freshly prepared zeolite EU-1 ("freshly prepared" means the product of synthesis and washing, with optional drying, as hereinafter described) and also forms of it resulting from dehydration, and/or calcination, and/or ion exchange. In freshly prepared zeolite EU-1, R may include an alkali metal cation; especially sodium, and/or ammonium, and usually or when prepared from alkylated nitrogen compounds, includes nitrogen-containing organic cations as described below or cationic degradation products thereof, or precursors thereof. These nitrogen containing cations are hereinafter referred to as Q.

The freshly prepared zeolite EU-1 may also contain nitrogen-containing compounds well in excess of the 1.5 moles set out in the aforesaid definition of the composition of zeolite EU-1, typically in the range 0.1 to 20 moles per mole of $Y_2O_3$. Since EU-1 is a zeolite, the excess nitrogen-containing base must be physically trapped within the crystal lattice, because it is too large to escape. It can only be removed by thermal or oxidative degradation. This physically trapped basic material does not constitute part of the composition for the purposes of the definition. Thus a zeolite EU-1 as made typically has the following molar composition:

0 to 0.8 $M_2O$:0.1 to 20 $Q:Y_2O_3$:10 to 500 $XO_2$:0 to 100 $H_2O$ wherein M is an alkali metal or ammonium, and $M_2O+Q \geq 1.0$ The $H_2O$ content of freshly prepared zeolite EU-1 depends on the conditions in which it has been dried after synthesis.

In calcined forms of zeolite EU-1, R may be alkali metal but includes less or no nitrogen-containing organic compounds, since these are burnt out in the presence of air, leaving hydrogen as the other balancing cation.

Among the ion-exchanged forms of zeolite EU-1 the ammonium ($NH_4^+$) is of importance since it can be readily converted to the hydrogen form by calcination. The hydrogen form can also be prepared directly by exchange with an acid. The hydrogen-form and forms containing metals introduced by ion exchange are described further below.

We believe that zeolite EU-1 is similar to the ZSM-23 family of zeolites (as described for example, in U.S. Pat. No. 4,076,842, although our attempts to make ZSM-23 in accordance with this and other published descriptions have so far been unsuccessful). An analogy can be cates made by dissolving silica in an alkali metal hydroxide or quaternary ammonium hydroxide or a mixture thereof.

The alumina source is most conveniently sodium aluminate, but aluminium, an aluminium salt, for example the chloride, nitrate or sulphate, an aluminium alkoxide or alumina itself, which should preferably be in a hydrated or hydratable form such as colloidal alumina, pseudohoehmite, boehmite, gamma alumina or the alpha or beta trihydrate.

The reaction mixture is usually reacted under autogenous pressure, optionally with added gas, e.g. nitrogen, at a temperature between 85° and 250° C. until crystals of zeolite EU-1 form, which can be from 1 hour to many months depending on the reactant composition and the operating temperature. Agitation is optional, but is preferable since it reduces the reaction time.

At the end of the reaction, the solid phase is collected on a filter and washed and is then ready for further steps such as drying, dehydration and ion-exchange.

If the product of the reaction contains alkali metal ions, these have to be at least partly removed in order to prepare the hydrogen form of EU-1 and this can be done by ion exchange with an acid, especially a strong mineral acid such as hydrochloric acid or by way of the ammonium compound, made by ion exchange with a solution of an ammonium salt such as ammonium chloride. Ion exchange can be carried out by slurrying once or several times with the ion-exchange solution. The zeolite is usually calcined after ion exchange but this may be effected before ion-exchange or during ion-exchange if the latter is carried out in a number of stages.

In general, the cation(s) of zeolite EU-1 can be replaced by any cation(s) of metals, and particularly those in Groups IA, IB, IIA, IIB, III (including rare earths) VIII (including noble metals) and by lead, tin and bismuth. (The Periodic Table is as in "Abridgements of Specifications" published by the UK Patent Office). Exchange is carried out using any water soluble salts containing the appropriate cation.

When used as a catalyst, zeolite EU-1 can be associated with an inorganic matrix, which can be either inert or catalytically active. The matrix may be present simply as a binding agent to hold the small zeolite particles (0.005 to 10 microns) together, or it may be added as a diluent to control the amount of conversion in a process which may otherwise proceed at too high a rate, leading to catalyst fouling as a result of excessive coke formation. Typical inorganic diluents include catalyst support materials such as alumina, silica and kaolinic clays, bentonites, montmorillonites, sepiolite, attapulgite, Fullers earth, synthetic porous materials such as $SiO_2$—$Al_2O_3$, $SiO_2$—$ZrO_2$, $SiO_2$—$ThO_2$, $SiO_2$—$BeO$, $SiO_2$—$TiO_2$ or any combination of these diluents. An effective way of mixing zeolite EU-1 with such diluents is to mix appropriate aqueous slurries in a mixing nozzle and then to spray-dry the slurry. Other ways of mixing can be used.

If zeolite EU-1 in any cationic form or as a catalytic composite is exchanged or impregnated with hydrogenation/dehydrogenation components, such as Ni, Co, Pt, Pd, Re, Rh, hydrocracking and reforming catalysts can be made, especially if the $Na_2O$ content is less than 0.1% w/w.

A wide range of hydrocarbon conversion catalysts can be prepared from zeolite EU-1 by ion exchange or impregnation with cations, or oxides, selected from the following, Cu, Ag, Mg, Ca, Sr, Zn, Cd, B, Al, Sn, Pb, V, P, Sb, Cr, Mo, W, Mn, Re, Fe, Co, Ni, noble metals.

Usually the EU-1 catalyst will be in acid form, thus stoichiometry is maintained by $H^+$ or $H_3O^+$ as an additional balancing cation, or as sole cation. Such catalysts may find application in the following processes; catalytic cracking, hydrodesulphurization, hydrodenitrification, catalytic dewaxing, alkylation of alkanes or aromatics, dealkylation, disproportionation, isomerisation of alkanes and alkyl benzenes, dehydration reactions, oxidation and polymerisation.

We have found that zeolite EU-1 is especially useful as a catalyst for xylenes isomerisation. As is well known, the major aim in xylenes isomerisation is to increase the para-xylene content of the feedstock at the expense of other isomers since para-xylene is a particularly useful and valuable product. The mixed xylenes feedstocks commonly available for xylenes isomerisation usually contain amounts of the three xylene isomers as well as ethylbenzene. Hitherto, some of the mixed xylenes feedstock available has contained relatively small amounts of ethylbenzene but it is anticipated that in the future such feedstocks will become more expensive and that resort will have to be made to feedstocks containing rather larger amounts of ethylbenzene, say up to about 25% ethylbenzene.

According to a further aspect of the present invention we provide a hydrocarbon conversion process which comprises contacting an alkylbenzene or a mixture of alkylbenzenes under isomerisation conditions in the vapour or liquid phase with a catalyst comprising EU-1.

The EU-1 zeolite may conveniently be used as an aggregate in the form of pellets or extrudates, and a dispersing medium, for example gamma-alumina, may be used in the aggregates.

In the vapour phase suitable isomerisation conditions include a temperature in the range 100°–600° C., preferably 200°–450° C., a pressure in the range 0.5–50, preferably 1–5 atm abs, and a weight hourly space velocity (WHSV) up to 80, or even higher if desired. These conditions are used preferably in the absence of added free hydrogen and with EU-1 containing no hydrogenation/dehydrogenation component.

In the liquid phase suitable isomerisation conditions include a temperature in the range 0°–350° C., a pressure in the range 1–200, preferably 5–70 atm abs., and, in a flow system, a weight hourly space velocity (WHSV) preferably in the range 1 to 30, the higher flow rates being used at the higher temperature. Optionally a diluent is present, suitably one or more of those having a critical temperature higher than the isomerisation temperature being used and including toluene, trimethylbenzene, naphthenes and paraffins. Preferably the diluent if present amounts to 1–90% w/w of the feed to the isomerisation reaction. In this liquid phase process the catalyst also preferably contains no hydrogenation/dehydrogenation component and no added free hydrogen is present.

Optionally isomerisation in the vapour phase is conducted in the presence of hydrogen. A suitable mole ratio of hydrogen to alkylbenzene lies in the range 3 to 30:1. If hydrogen is used, the catalyst should comprise a hydrogenation/dehydrogenation component, preferably a metal of Group VIII of the Periodic Table, especially platinum or nickel. The amount of metal preferably lies in the range 0.1 to 2% w/w on the total catalyst. If desired, the catalyst may contain one or more additional metals, for example, rhenium, suitably in the range 0.1 to 2% w/w on the total catalyst.

Preferably the alkylbenzene is a xylene, for example, m-xylene for conversion to p-xylene, or a mixture of xylenes, possibly with ethylbenzene. The amount of ethylbenzene present will depend to some extent on the source of the xylene mixture but will usually lie in the range 0 to 25% w/w, especially 6 to 25% w/w of the feedstock, since the process is able to handle feeds containing relatively high amounts of ethylbenzene.

If desired, the EU-1 catalyst used in the process of the invention may contain small amounts of alkali metal, for example up to 1000 and especially up to 300 ppm w/w as equivalent $Na_2O$. It appears to be unnecessary to have present ions other than hydrogen and (for hydroisomerisation) Goup VIII metal ions. The EU-1 may contain onium compounds and their decomposition products to the extent of 0.05 to 1.0% w/w such as are present after substantial removal of such materials by calcination in air, when it is to be used in xylenes isomerisation.

Zeolite EU-1 may also find applications in the separation of aromatics and cycloparaffins, and in pollution control by its ability to remove organic contaminants from aqueous effluents.

The invention is illustrated by the following Examples.

EXAMPLE 1

Preparation of sodium hexamethonium EU-1 and sodium hydrogen EU-1

The synthesis mixture had the following molar composition:

| | |
|---|---|
| $Na_2O$ | 7.5 |
| $HxBr_2$ | 7.5 |
| $Al_2O_3$ | 1.0 |
| $SiO_2$ | 43 |
| $H_2O$ | 2220 |

Hx $Br_2$ = hexamethonium bromide = $Me_3N(CH_2)_6$-$NMe_3{}^{2+}(Br^-)_2$ Solid silica (36 g of AKZO grade KS 300 of composition 5.09 $Na_2O$, $Al_2O_3$, 728 $SiO_2$, 248 $H_2O$) was suspended in a mixture of 34 g hexamethonium bromide and 468 g water. Next 6 g solid sodium hydroxide, and 2.8 g solid sodium aluminate (1.25 $Na_2O$, $Al_2O_3$, $3H_2O$) were dissolved in 35 g water and stirred into the silica suspension. The resulting slurry was reacted in a stainless steel autoclave stirred at 800 rpm for 22.5 hours at 200° C. under autogenous pressure. After cooling to about 60° C., the slurry product was filtered and washed with 2 liters of distilled water at 60° C., and dried overnight at 120° C. The product was sodium hexamethonium EU-1, along with a small quantity of alphaquartz, had the X-ray data shown in Table 1, and the composition 0.8 $Na_2O$, 5.5 Q, $Al_2O_3$, 35 $SiO_2$, 10 $H_2O$ where $Q^{2+}$ is hexamethonium i.e. for correct stoichiometry $\frac{1}{2}[O[(CH_3)_3N-(CH_2)_6-N(CH_3)_3]_2O]$, and crystallite sizes of 1 to 3 microns.

This product was calcined in air for 48 hours at 450° C. and was found to have an X-ray diffraction pattern as shown in Table 2 and a nitrogen and carbon content of less than 0.1% w/w. This product was sodium hydrogen EU-1.

EXAMPLE 2

Preparation of hydrogen EU-1

The calcined product of Example 1 was slurry-exchanged for 1 hour at 25° C. with 3.6 ml of N hydrochloric acid per g. of zeolite. The resulting hydrogen EU-1 zeolite was washed with 10 ml distilled water per g. of zeolite, dried over-night at 120° C. and activated for sorption and catalyst testing at 450° C., for 6 hours.

EXAMPLES 3–11

The synthesis procedure of Example 1 was repeated using a range of reactants, mixture compositions, reaction temperatures and reaction times. The results are shown in Table 4.

TABLE 4

| Ex. | Organic Component | Silicon Component | Reaction Mixture Composition - moles | | | | | Temp °C. | Time hours | Product |
|---|---|---|---|---|---|---|---|---|---|---|
| | | | $Na_2O$ | Q | $Al_2O_3$ | $SiO_2$ | $H_2O$ | | | |
| 3 | $HxBr_2$ | KS 300 | 10 | 10 | 1 | 60 | 1000 | 180 | 168 | major EU-1 (1) |
| 4 | $HxBr_2$ | KS 300 | 10 | 10 | 1 | 86 | 3000 | 150 | 168 | major EU-1 (2) |
| 5 | $HxBr_2$ | CAB-O-SIL M5 | 20 | 20 | 1 | 120 | 6000 | 180 | 168 | major EU-1 |
| 6 | $HxBr_2$ | CAB-O-SIL M5 | 10 | 10 | 1 | 60 | 3000 | 220 | 3.75 | major EU-1 |
| 7 | $HxCl_2$ | KS 300 | 7.5 | 7.5 | 1 | 45 | 2200 | 200 | 22 | major EU-1 (3) |
| 8 | $HxCl_2$ | KS 300 | 7.5 | 7.5 | 1 | 45 | 2200 | 200 | 39 | major EU-1 (3) |
| 9 | $HxBr_2$ | CAB-O-SIL M5 | 10 | 10 | 1 | 60 | 3000 | 200 | 6.5 (4) | major EU-1 |
| 10 | $HxBr_2$ | CAB-O-SIL M5 | 10 | 10 | 1 | 60 | 3000 | 200 | 4.0 (5) | major EU-1 |
| 11 | $HxBr_2$ | CAB-O-SIL M5 | 10 | 10 | 1 | 60 | 2000 | 200 | 8 | major EU-1 |
| 12 | $HxBr_2$ | CAB-O-SIL M5 | 10 + 10 (6) | 10 | 1 | 60 | 3000 | 180 | 5 | major EU-1 + tracea-quartz |
| 13 | $HxBr_2$ | CAB-O-SIL M5 | 10 | 7 + 3 (7) | 1 | 60 | 3000 | 180 | 5 | major EU-1 + tracea-quartz |

Notes on Table 4
$HxBr_2$ = hexamethonium bromide
$HxCl_2$ = hexamethonium chloride
KS 300 = silica (AKZO grade KS 300)
CAB-O-SIL M5 = silica (Cabot Carbon Fume silica)
(1) EU-1 product $SiO_2/Al_2O_3$ = 45.7
(2) EU-1 product $SiO_2/Al_2O_3$ = 76.8
(3) EU-1 product $SiO_2/Al_2O_3$ = 32.0
(4) Stirrer speed 300 rpm
(5) Stirrer speed 750 rpm
(6) 10 moles $Na_2O$ + 10 moles $NH_4OH$
(7) 7 moles $HxBr_2$ + 3 moles hexamethylene diamine

EXAMPLE 14

Example 3 was repeated except that hexamethonium bromide was replaced by a chemical equivalent of decamethonium bromide. The product after 150 hours at 180° C. was zeolite EU-1 plus minor amounts of an unknown crystalline impurity.

EXAMPLES 15-17

A sample of zeolite EU-1 (prepared as described in Example 1) was formed into aggregates of 425 to 1000 μm. Three samples of aggregates (Examples 15-17) were tested as xylenes isomerisation catalysts as follows:

Each sample was charged to a glass reactor and heated in a stream of air at 500° C. for 16 hours. It was then cooled in a nitrogen stream to reaction temperature. A feedstock consisting mainly of aromatic hydrocarbons was then passed over the sample at atmospheric pressure for 6 hours.

For comparison, (Example A) a 12 g sample of an amorphous silica/alumina catalyst in the form of 3-5 mm beads containing 10% alumina was charged to a glass reactor and treated in the same manner.

The composition of the feedstock is shown in Table 5. The reaction conditions used and the product composition after 6 hours on line are shown for each sample of EU-1 and for the silica/alumina catalyst in Table 6.

TABLE 5

| Component | Weight (%) |
|---|---|
| Benzene | 0.02 |
| Toluene | 1.87 |
| Ethylbenzene | 8.56 |
| Para-xylene | 7.63 |
| Meta-xylene | 50.58 |
| Ortho-xylene | 26.02 |
| $C_9$ + aromatics | 3.91 |

TABLE 6

| | Example | | | |
|---|---|---|---|---|
| | 15 | 16 | 17 | A |
| Catalyst | EU-1 | EU-1 | EU-1 | $SiO_2/Al_2O_3$ |
| Temperature (°C.) | 450 | 450 | 400 | 450 |
| WHSV | 13 | 84 | 59 | 1 |
| Product Composition (wt %) | | | | |
| Benzene | 0.69 | 0.20 | 0.10 | 0.53 |
| Toluene | 3.69 | 2.06 | 2.03 | 4.19 |
| Ethylbenzene | 6.67 | 8.34 | 8.35 | 7.46 |
| Para-xylene | 19.75 | 19.65 | 17.22 | 17.28 |
| Meta-xylene | 42.51 | 43.58 | 44.38 | 41.90 |
| Ortho-xylene | 19.39 | 20.82 | 22.46 | 20.78 |
| $C_9$ + aromatics | 6.41 | 4.11 | 4.08 | 6.59 |
| % Ethylbenzene loss | 22.1 | 2.6 | 2.4 | 12.8 |
| % Xylene loss | 3.1 | 0.2 | 0.2 | 5.1 |

Referring to Table 6, Example 15 shows that EU-1 catalyst can produce a higher percentage of para-xylene in the product, a greater ethylbenzene loss and less xylenes destruction at a higher space velocity than the amorphous silica/alumina catalyst (Comparative Example A).

Example 16 shows that a higher space velocity EU-1 catalyst can still give a high percentage of para-xylene in the product with very little xylenes loss.

Example 17 shows that at a 50° C. lower reaction temperature and a much higher space velocity than that used in Example 16, EU-1 catalyst can still give the same percentage of para-xylene in the product as does the silica/alumina catalyst but with very little xylenes loss.

What we claim is:

1. Zeolite EU-1 having a molar composition expressed by the formula:

0.5 to 1.5 $R_2O:Y_2O_3$:at least 10 $XO_2$:0 to 100 $H_2O$ wherein R is a monovalent cation or $1/n$ of a cation of valency n, X is silicon and/or germanium, Y is one or more of aluminium, iron, gallium or boron, and $H_2O$ is water of hydration additional to water notionally present when R is H, and having, when freshly prepared, an X-ray diffraction pattern as shown in Table 1.

2. Zeolite EU-1 according to claim 1 wherein the molar composition is expressed by the formula:

0.5 to 1.5 $R_2O:Y_2O_3$:20 to 300 $XO_2$:0 to 100 $H_2O$.

3. Zeolite EU-1 according to claim 1 or claim 2 wherein R is or includes hydrogen.

4. Zeolite EU-1 according to claim 1 as freshly made having a molar composition expressed by the formula:

0 to 0.8 $M_2O$:0.1 to 20 $Q:Y_2O_3$:10 to 500 $XO_2$:0 to 100 $H_2O$ wherein M is an alkali metal or ammonium, Q is a nitrogen-containing organic cation and $M_2O+Q \geqq 1.0$.

5. A method of making zeolite EU-1 as defined in claim 1 which comprises reacting an aqueous mixture comprising at least one oxide $XO_2$, at least one oxide $Y_2O_3$ and at least one alkylated derivative of a polymethylene α-ω diamine having the formula:

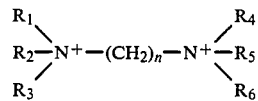

, or a precursor thereof, wherein n is in the range from 3 to 12 and $R_1$ to $R_6$ which may be the same or different, can be alkyl or hydroxyalkyl groups containing from 1 to 8 carbon atoms and up to five of the groups $R_1$–$R_6$ can be hydrogen, the mixture having the molar composition:

| $XO_2/Y_2O_3$ | at least 10 |
|---|---|
| $OH^-/XO_2$ | 0.1 to 6.0 |
| $(M^+ + Q)/Y_2O_3$ | 0.5 to 100 |
| $Q/(M^+ + Q)$ | 0.1 to 1.0 |
| $H_2O/XO_2$ | 1 to 100 | where X is silicon and/or germanium, Y is one or more of aluminium, iron, gallium, or boron, M is an alkali metal or ammonium, and Q is the aforesaid alkylated derivative of a polymethylene diamine, or a precursor thereof.

6. A method according to claim 5 wherein $XO_2/Y_2O_3$ is in the range 10 to 150.

7. A method according to claim 5 or claim 6 wherein $OH^-/XO_2$ is in the range 0.1 to 1.0.

8. A method according to claim 5 wherein the alkylated derivative of a polymethylene diamine is an alkylated hexamethylene diamine.

9. A method according to claim 8 wherein the alkylated hexamethylene diamine is an N, N, N, $N^1$, $N^1$, $N^1$-hexamethyl-1,6-hexamethylene diammonium salt.

10. A catalyst comprising zeolite EU-1 having a molar composition expressed by the formula:

0.5 to 1.5 $R_2O:Y_2O_3$:at least 10 $XO_2$:0 to 100 $H_2O$ wherein R is a monovalent cation or 1/n of a cation of valency n, X is silicon and/or germanium, Y is one or more of aluminum, iron, gallium or boron, and $H_2O$ is water of hydration additional to water notionally present when R is H, and having, when freshly prepared, an X-ray diffraction pattern as shown in Table 1.

11. A catalyst according to claim 10 wherein the molar composition is expressed by the formula:

0.5 to 1.5 $R_2O:Y_2O_3$:20 to 300 $XO_2$:0 to 100 $H_2O$.

12. A catalyst according to claim 10 or claim 15 wherein R is or includes hydrogen.

13. A catalyst according to claim 10 comprising zeolite EU-1 as freshly made having a molar composition expressed by the formula:

0 to 0.8 $M_2O$:0.1 to 20 $Q:Y_2O_3$:10 to 500 $XO_2$:0 to 100 $H_2O$ wherein M is an alkali metal or ammonium, Q is a nitrogen-containing organic cation, and $M_2O + Q \geqq 1.0$.

* * * * *